United States Patent
Mulhauser et al.

(10) Patent No.: US 6,267,772 B1
(45) Date of Patent: Jul. 31, 2001

(54) IMPLANTABLE PROSTHESIS

(75) Inventors: Paul J. Mulhauser, New York, NY (US); Paul C. DiCesare, Norwalk, CT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/291,651

(22) Filed: Apr. 6, 1999

Related U.S. Application Data

(62) Division of application No. 08/250,657, filed on May 27, 1994, which is a continuation of application No. 07/886,689, filed on May 20, 1992, now abandoned.

(51) Int. Cl.⁷ .............................. A61B 17/00; A61F 2/00
(52) U.S. Cl. ......................................... 606/151; 623/11.11
(58) Field of Search ................................ 623/1.21, 11.11; 606/108, 193, 151; 424/426, 424; 602/46, 904, 44, 58

(56) References Cited

U.S. PATENT DOCUMENTS

| | | |
|---|---|---|
| 2,671,444 | 3/1954 | Pease, Jr. . |
| 3,054,406 | 9/1962 | Usher . |
| 3,646,615 | 3/1972 | Ness . |
| 4,007,743 | 2/1977 | Blake . |
| 4,347,847 | 9/1982 | Usher . |
| 4,452,245 | 6/1984 | Usher . |
| 4,548,202 | 10/1985 | Duncan . |
| 4,561,434 | 12/1985 | Taylor . |
| 4,633,873 | 1/1987 | Dumican et al. . |
| 4,655,221 | 4/1987 | Devereux . |

(List continued on next page.)

FOREIGN PATENT DOCUMENTS

| | | |
|---|---|---|
| 2114282 | 7/1994 | (CA) . |
| 0 362 113 | 4/1990 | (EP) . |
| WO 90/14796 | 12/1990 | (WO) . |
| WO 93/17635 | 9/1993 | (WO) . |
| WO 96/09795 | 4/1996 | (WO) . |

OTHER PUBLICATIONS

Gregory L. Brown, M.D. et al., "Comparison of Prosthetic Materials for Abdominal Wall Reconstruction in the Presence of Contamination and Infection", Annals of Surgery, Jun. 1985, vol. 201, pp. 705–711.

Scott D. Jenkins, M.D. et al., "A Comparison of Prosthetic Materials Used to Repair Abdominal Wall Defects", Surgery, Aug. 1983, vol. 94, No. 2, pp. 392–398.

"Prevention of Postsurgical Adhesions by Interceed (TC7)", Fertility and Sterility, Jun. 1989, vol. 51, No. 6, pp. 933–938.

Hernando Cordona, M.D., "Prosthokeratoplasty", 1983, Cornea, vol. 2, No. 3, 1983. pp. 179–183.

Alonzo P. Walker, M.D. et al., "Double–Layer Prostheses for Repair of Abdominal Wall Defects in a Rabbit Model", pp 32–37, Journal of Surgical Research, vol. 55, No. 1, Jul. 1993.

*Primary Examiner*—David J. Isabella
(74) *Attorney, Agent, or Firm*—Wolf, Greenfield & Sacks, P.C.

(57) ABSTRACT

An implantable prosthesis for occluding the opening of a muscle or tissue defect. The implant is laparoscopically deliverable with a system for loading and delivering the prosthesis through a trocar cannula. The prosthesis includes an implantable material with a body portion sufficient to extend across and occlude a defect opening. Antimigration barbs extend from the implantable material to prevent migration of the prosthesis after implantation. A semi-rigid ring may be attached to the material for supporting the body portion. The barbs may be located on the ring. The implantable prosthesis may be provided with a sufficient hoop strength to prevent the body portion from collapsing into the defect opening.

40 Claims, 11 Drawing Sheets

U.S. PATENT DOCUMENTS

| | | |
|---|---|---|
| 4,693,720 | 9/1987 | Scharnberg et al. . |
| 4,710,192 | 12/1987 | Liotta et al. . |
| 4,769,036 | 9/1988 | Modir . |
| 4,769,038 | 9/1988 | Bendavid . |
| 4,784,899 * | 11/1988 | Lazarus ............................ 623/1.14 |
| 4,796,603 | 1/1989 | Dahlke . |
| 4,854,316 | 8/1989 | Davis . |
| 4,865,026 | 9/1989 | Barrett . |
| 4,955,907 | 9/1990 | Ledergerber . |
| 5,002,572 | 3/1991 | Picha . |
| 5,006,106 | 4/1991 | Angelchik . |
| 5,059,205 | 10/1991 | El-Nounou et al. . |
| 5,104,399 * | 4/1992 | Lazarus ............................ 623/1.14 |
| 5,116,357 | 5/1992 | Eberach . |
| 5,122,155 | 6/1992 | Eberach . |
| 5,141,515 | 8/1992 | Eberach . |
| 5,147,374 | 9/1992 | Fernandez . |
| 5,147,387 | 9/1992 | Jansen . |
| 5,176,692 | 1/1993 | Wilk et al. . |
| 5,192,301 | 3/1993 | Kamiya et al. . |
| 5,195,542 | 3/1993 | Gazielly et al. . |
| 5,201,745 | 4/1993 | Tayot et al. . |
| 5,254,133 | 10/1993 | Seid . |
| 5,258,000 | 11/1993 | Gianturco . |
| 5,290,217 | 3/1994 | Campos . |
| 5,334,217 | 8/1994 | Das . |
| 5,350,399 | 9/1994 | Erlebacher et al. . |
| 5,356,432 | 10/1994 | Rutkow et al. . |
| 5,366,460 | 11/1994 | Eberbach . |
| 5,368,602 | 11/1994 | de la Torre . |
| 5,370,650 | 12/1994 | Tovey et al. . |
| 5,397,331 | 3/1995 | Himpens et al. . |
| 5,425,744 | 6/1995 | Fagan et al. . |
| 5,433,996 | 7/1995 | Kranzler et al. . |
| 5,451,235 | 9/1995 | Lock et al. . |
| 5,456,720 | 10/1995 | Schultz et al. . |
| 5,507,811 | 4/1996 | Koike et al. . |
| 5,593,441 | 1/1997 | Lichtenstein et al. . |
| 5,614,284 | 3/1997 | Kranzler et al. . |
| 5,634,931 | 6/1997 | Kugel . |
| 5,695,525 | 12/1997 | Mulhauser et al. . |
| 5,702,416 | 12/1997 | Kieturakis et al. . |
| 5,716,408 | 2/1998 | Eldridge et al. . |
| 5,743,917 | 4/1998 | Saxon . |
| 5,766,246 | 6/1998 | Mulhauser et al. . |
| 5,769,864 | 6/1998 | Kugel . |
| 5,836,961 | 11/1998 | Kieturakis et al. . |
| 5,916,225 | 6/1999 | Kugel . |

* cited by examiner

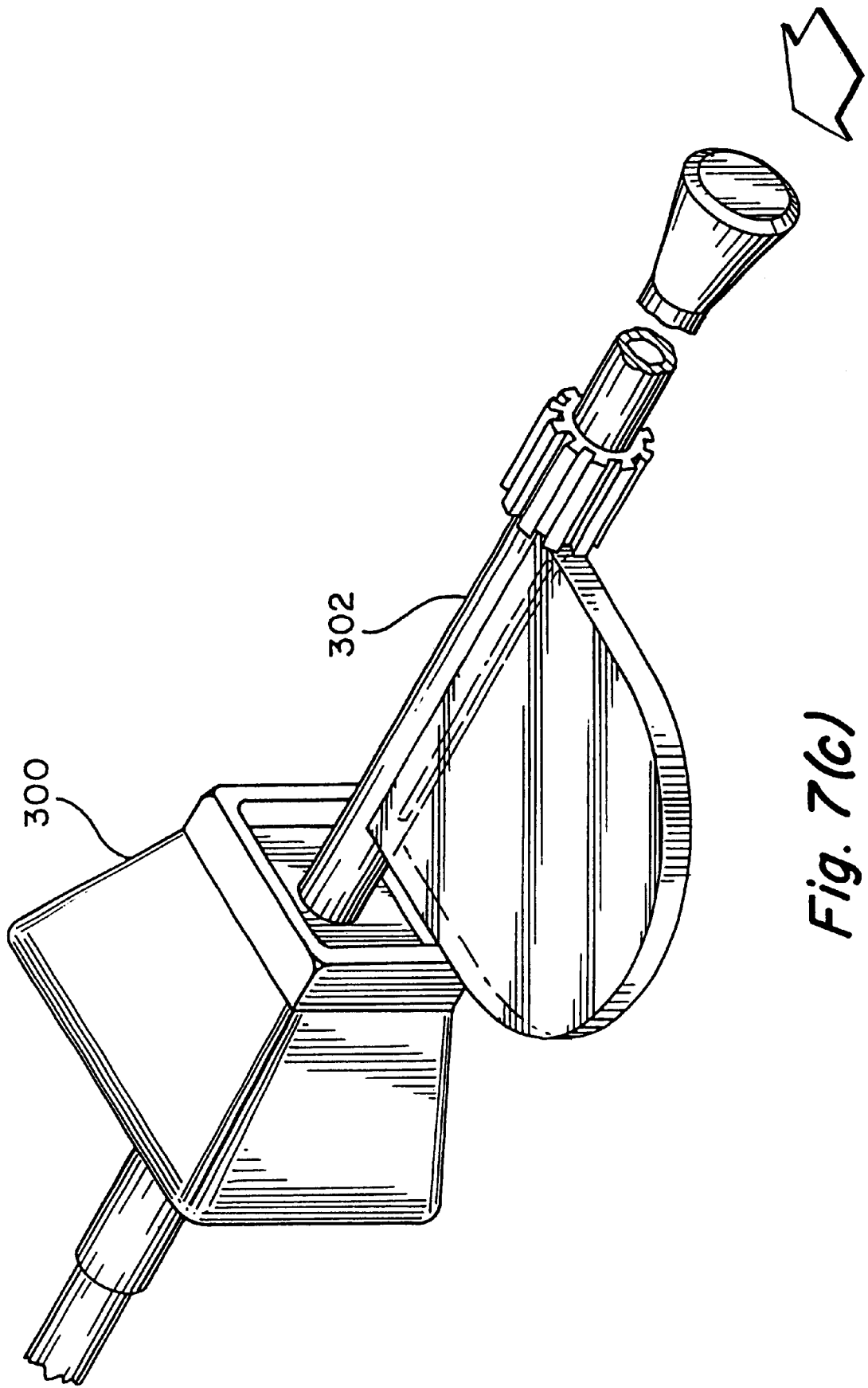

IMPLANTABLE PROSTHESIS

RELATED U.S. APPLICATION DATA

This application is a division of application Ser. No. 08/250,657, filed May 27, 1994, now pending, which is a continuation of application Ser. No. 07/886,689, filed May 20, 1992, now abandoned.

FIELD OF INVENTION

The present invention relates to an implantable prosthesis for occluding the opening of a muscle or tissue defect.

BACKGROUND OF THE INVENTION

Various implants have been proposed for repairing abdominal wall defects such as direct and indirect inguinal hernias. Inguinal hernias occur when the peritoneum (lining of the abdominal cavity) and bowel pass into the inguinal canal through a hole in the innermost muscle layer called the transversalis fascia. An indirect hernia forms when a portion of the intestine passes through the internal ring and courses obliquely down the inguinal canal. A direct hernia involves the rupture of the inguinal canal floor adjacent the internal ring. An indirect hernia is marked by a long tubeshaped defect while a direct hernia is identified by a shallow hole.

Classical repair of inguinal hernias (reparative herniorrhaphy) requires a two inch or longer incision through the abdominal wall. The many layers of healthy tissue are then retracted by the physician to expose the void. The healthy muscle and tissue which have been incised to reach the rupture site require a long period of recovery (six days or longer) and result in substantial postoperative pain.

A laparoscopic hernia repair technique recently proposed uses an illuminating optical instrument (laparoscope) which is inserted through a thin tube (trocar cannula) in the abdominal wall to visualize the interior of the abdominal cavity. The entire surgical procedure takes place using special surgical tools manipulated through additional cannulae extending through the abdominal wall. Laparoscopic surgery minimizes patient discomfort and recovery time, allows diagnosis without invasive surgery and lessens the risk of traumatic injury to the abdominal tissues.

Various mesh prostheses have been proposed for use in laparoscopic hernia repair. Representative are the mesh fabric logs or plugs 5 illustrated in FIG. 1 which are formed by rolling sheets of mesh into cylinders and then suturing the ends. The logs are inserted into the defect 6 until the void is filled. A larger flat piece of mesh 7, commonly referred to as an onlay patch, is placed over the herniated opening, holding the logs in place. The mesh materials become bound in place as tissue grows through the fabric.

The use of mesh logs or plugs may suffer from certain deficiencies. Overstuffing of the void may lead to occlusion of a testicular vessel and, potentially, testicular swelling or atrophy. Further, the mesh logs may cause a bulky protrusion which the patient can feel, although the sensation should decrease over time. Lastly, the use of customized plugs and logs does not lend itself to a standardized surgical procedure.

A composite mesh prosthesis suitable for use in classical and laparoscopic surgery is disclosed in commonly assigned U.S. Pat. No. 5,593,441 issued to Lichtenstein et al., entitled "Method For Limiting The Incidence Of Postoperative Adhesions", the disclosure of which is specifically incorporated herein by reference. The composite implant includes a tissue infiltratable fabric and an adhesion barrier which isolates the inflammatory mesh from sensitive tissue such as the abdominal viscera.

Various tools have been proposed in the art for loading and delivering the mesh implants through the trocar cannula and into the abdominal cavity. In the case of the mesh logs, typically one end of the log is held by a grasper which is then retracted into the lumen of an introducer tube. The rear-end loaded introducer and grasper are inserted into and through the trocar cannula. That technique may have certain disadvantages including the need to coordinate a separate introducer and grasper instrument to collapse the implant and then deliver the implant to the hernia site.

Accordingly, the prior art lacks a mesh implant suitable for laparoscopic repair which effectively occludes the hernia defect without stuffing the void. The prior art also lacks a single and efficient tool for collapsing and delivering an implant through a trocar cannula to a defect site.

SUMMARY OF THE INVENTION

The present invention is a prosthesis that may be laparoscopically implanted with a system for loading and delivering the prosthesis through a laparoscopic cannula. The implantable prosthesis is formed of a biologically compatible, flexible implantable material suitable for reinforcing tissue and closing tissue defects, particularly in the abdominal cavity. The prosthesis may include a semi-rigid ring which supports the material in a predetermined shape, improving handleability. The ring also imparts sufficient hoop strength to the implant, preventing the material from collapsing into the rupture site after emplacement.

In one embodiment of the invention, the implant includes a piece of knitted polypropylene monofilament mesh fabric having antimigration barbs extending therefrom to prevent movement of the implant as the tissue grows through the mesh. The mesh fabric may be attached to a ring of polypropylene with the antimigration barbs located on the bottom of the ring.

In another embodiment of the invention, spaced portions of mesh extend beyond the ring providing sites for stapling to healthy tissue surrounding the herniated area.

In a further embodiment, the mesh is covered with a barrier material which isolates the inflammatory fabric from sensitive tissue such as the abdominal viscera. The edges of the barrier material overlying the mesh fabric are liftable, allowing the underlying anchoring portions of mesh to be secured to neighboring tissue.

The present invention also includes a device for loading and delivering the mesh implant to a trocar cannula emplaced in the abdominal cavity. A main body is provided with a lumen for reducing the implant into a narrower cylindrical configuration. An introducer shaft winds the implant within the lumen and then advances the collapsed implant from the delivery tool, through the trocar cannula and into the abdominal cavity. A cartridge holds the prosthesis in its normal expanded configuration until the surgeon is ready to implant the device.

It is among the general objects of the invention to provide a mesh implant which is suitable for laparoscopic herniorrhaphy.

It is a further object of the invention to provide a mesh implant for repairing direct and indirect inguinal hernias.

It is a further object of the invention to provide a mesh implant which reduces the incidence of postoperative adhesions.

An additional object of the invention is to provide an instrument for loading and delivering the mesh implant at the surgical site.

Other objects and features of the present invention will become apparent from the following detailed description when taken in connection with the accompanying drawings which disclose multiple embodiments of the invention. It is to be understood that the drawings are designed for the purpose of illustration only and are not intended as a definition of the limits of the invention.

DESCRIPTION OF THE DRAWINGS

The foregoing and other objects and advantages of the invention will be appreciated more fully from the following drawings in which:

FIGS. 7(a)–(c) are schematic representations of a method of loading and delivering a mesh implant to repair an inguinal hernia.

DESCRIPTION OF THE PREFERRED EMBODIMENTS

Figure 1:
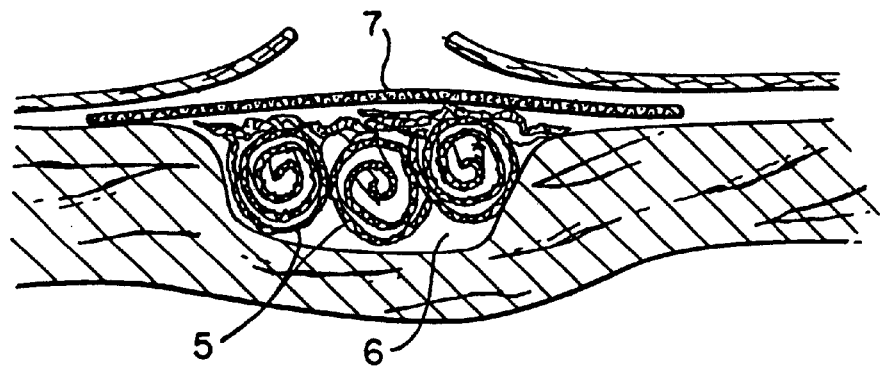
FIG. 1 is an illustration of prior art mesh logs or plugs used to repair direct and indirect inguinal hernias.
Figure 2A:
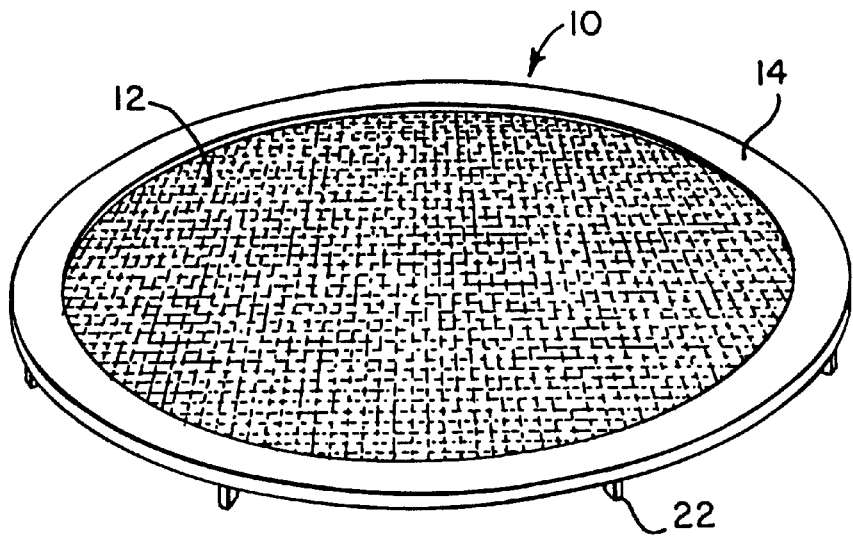
FIG. 2(a) is an illustration of the implant in accordance with the present invention.
Figure 2B:
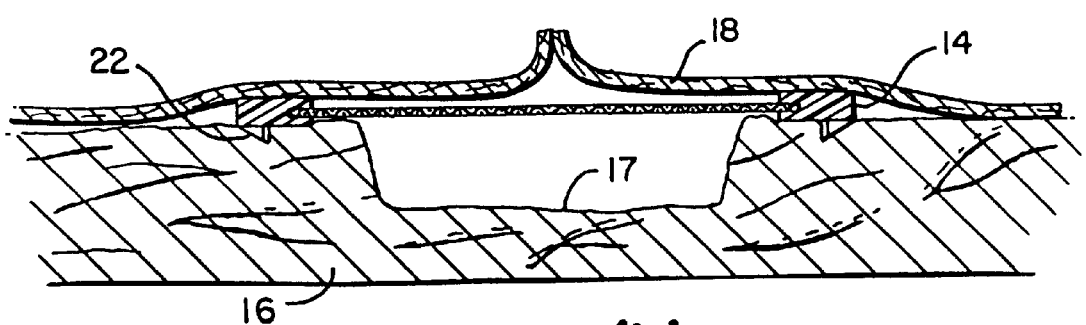
FIG. 2(b) is an illustration of a preperitoneal repair using the mesh implant shown in FIG. 2(a)
Figure 3A:
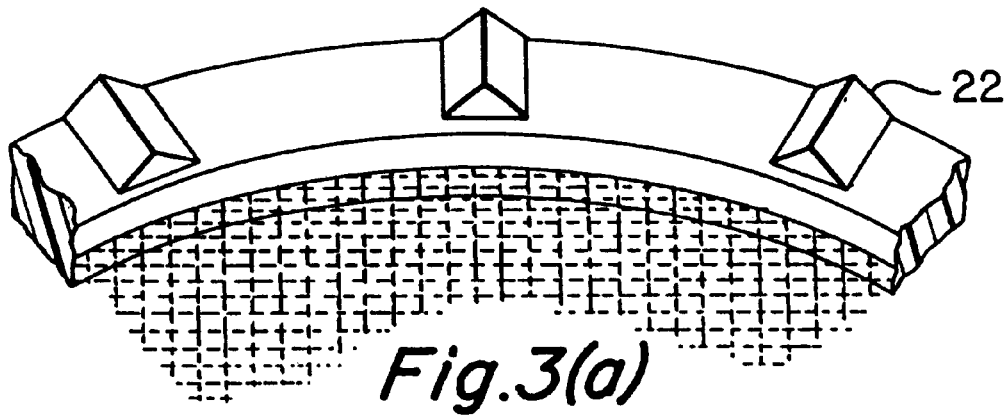
FIGS. 3(a)–(i) are illustrations of variously shaped anti-migration barbs for preventing movement of the implant.
Figure 3B:
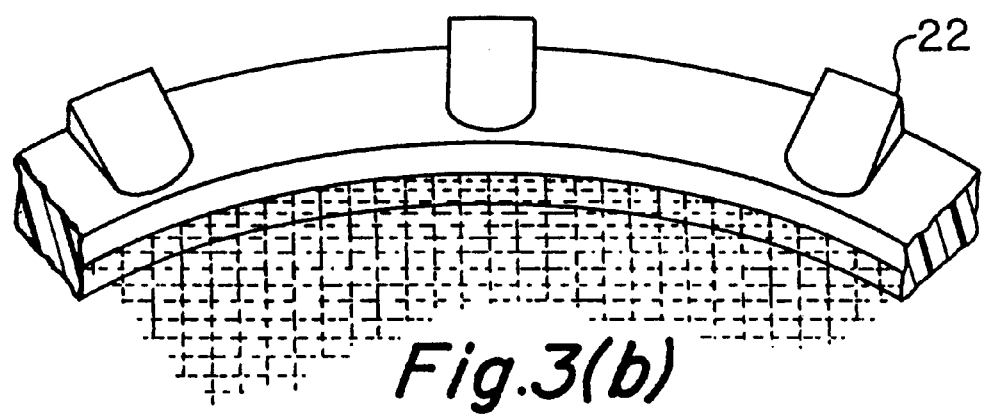
Figure 3C:
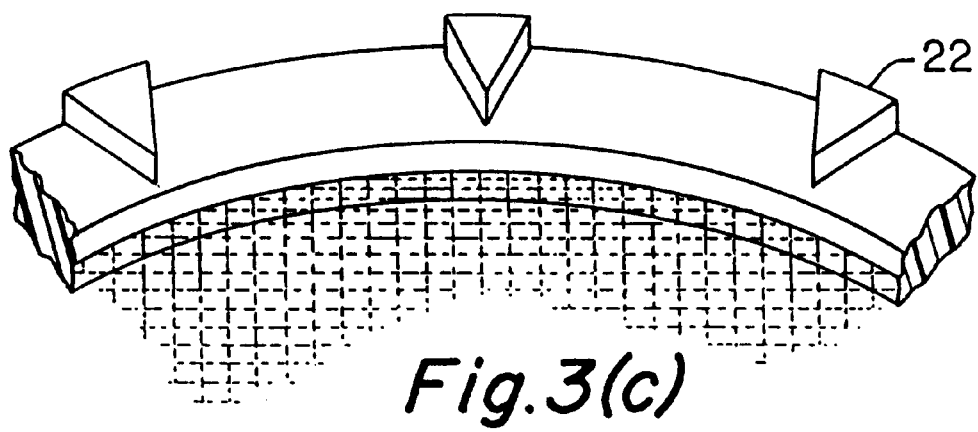
Figure 3D:
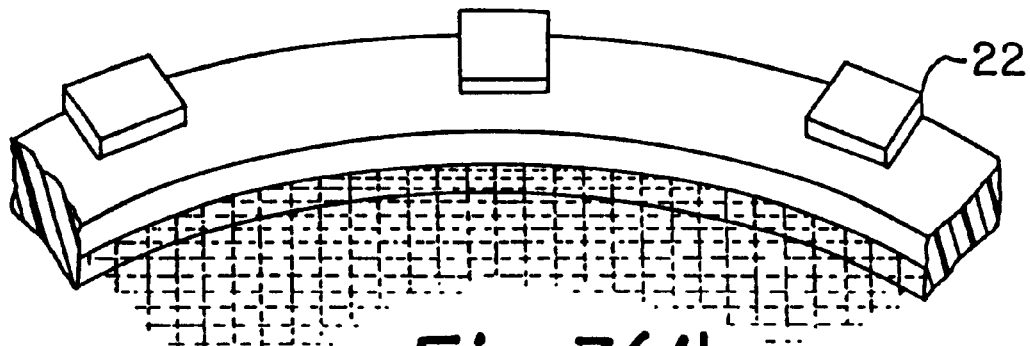
Figure 3E:
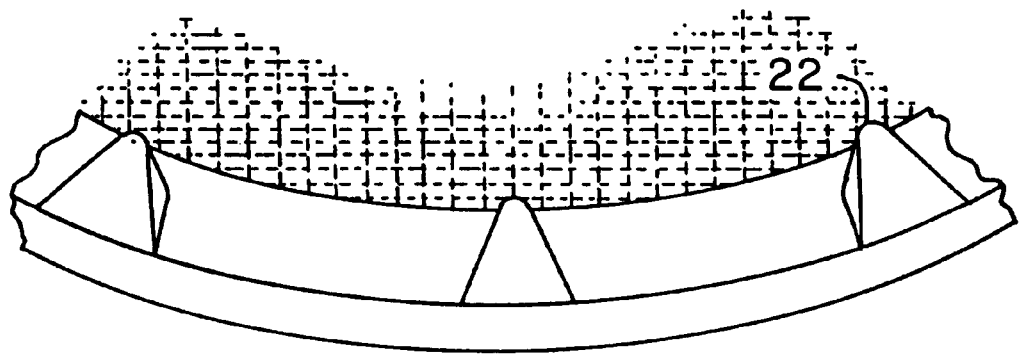
Figure 3F:
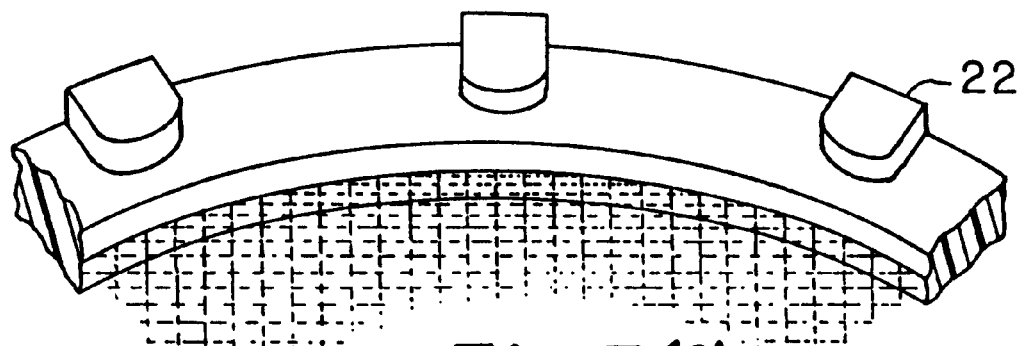
Figure 3G:
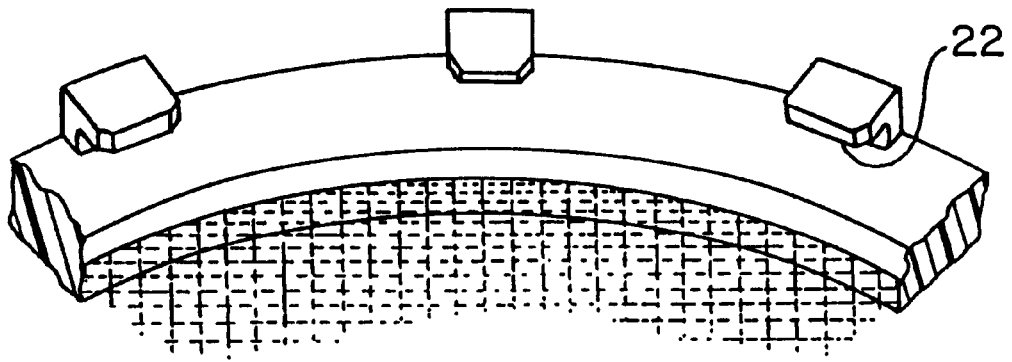
Figure 3H:
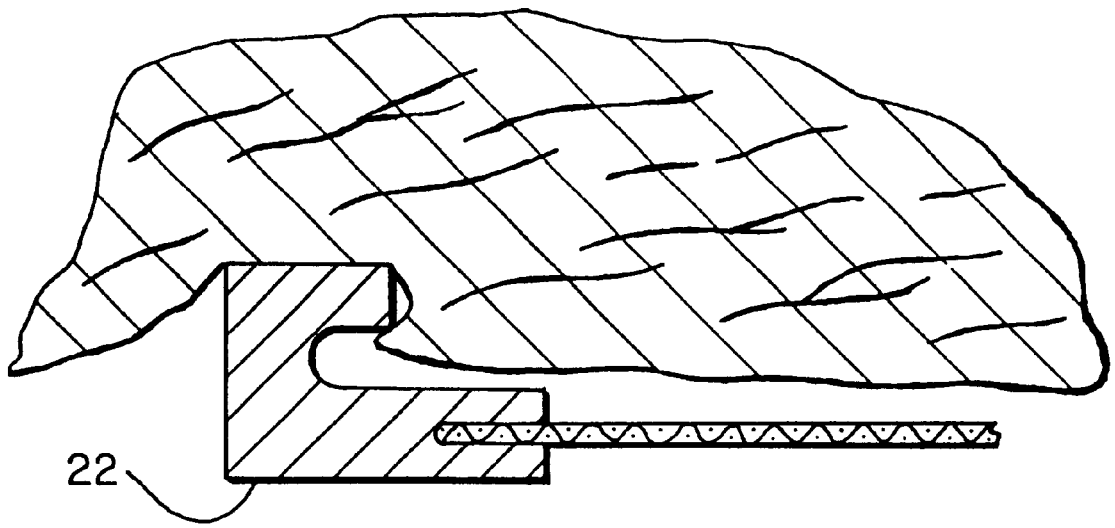
Figure 3I:
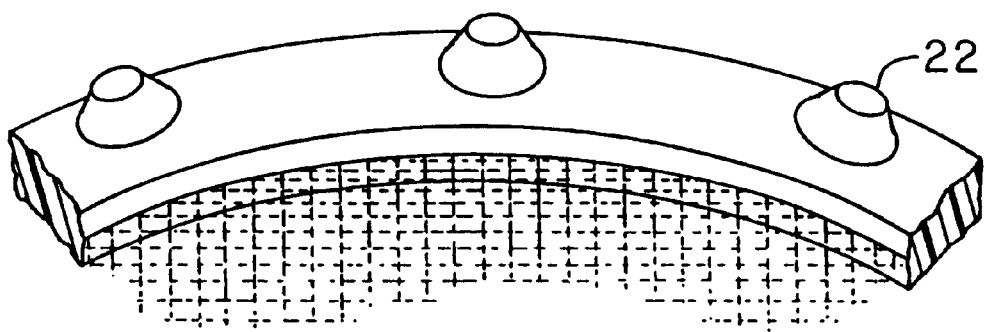

The implantable prosthesis 10 for repairing and reinforcing a ruptured or defective muscular wall illustrated in FIGS. 2(a)–2(b) includes a pliable tissue infiltratable fabric 12 and a semi-rigid frame 14. The fabric includes a plurality of openings which allow sufficient tissue ingrowth to secure the prosthesis to healthy tissue surrounding the defect site. The frame or skeleton is more rigid than the fabric and maintains the prosthesis in a predetermined shape, improving the handleability of the mesh implant at the surgical site. The frame also may provide the implant with a sufficient hoop strength to prevent the mesh fabric from collapsing into the defect. In the repair of inguinal hernias, the semi-rigid frame seats against the sound abdominal tissue 16 surrounding the defect 17, the tissue infiltratable fabric extending across the opening of the hernia without filling the void. In the preperitoneal procedure illustrated, the implant 10 is anchored under the peritoneum 18.

The relatively flat implant is sufficiently pliable to allow the surgeon to roll the implant into a narrow cylinder which is suitable for loading into the lumen of a trocar cannula. Upon deployment, the implant reverts back to its normal flat configuration. Alternatively, the unstressed implant may be formed with a slight convexity or concavity. The shape and size of the prosthesis, and of the respective fabric and frame, may vary according to the surgical application as would be apparent to those of skill in the art.

The tissue infiltratable fabric 12 includes a plurality of interstices or pores which are of sufficient size and orientation to allow tissue ingrowth. The frame has a predetermined shape and size sufficient to support the mesh relative to the herniated site, the frame sitting on the sound tissue surrounding the defect and the body portion of fabric extending completely across the opening of the defect. Preferably, the frame is ring-shaped, providing the implant with an inherent hoop strength which prevents the mesh from deflecting into the defect opening. The ring-shaped frame may be circular or elliptical, although alternative designs would include any shape which defines a boundary surrounding the opening of the hernia. For example, a square, diamond or hourglass configuration would be suitable so long as the ring surrounds the weakened area. The ring may be formed from a single element or, alternatively, from a series of spaced elements which together form a semi-rigid boundary about the body portion of the mesh fabric. Preferably, the ring has a rectangular cross-section, although other cross-sectional shapes would be suitable as would be apparent to those of skill in the art.

The rigidity of the ring relative to the mesh fabric stiffens the implant, improving handleability particularly when awkward surgical tools are being used to manipulate the implant. Thus, non-ring shaped frames, such as a criss-crossed arms configuration, would provide the necessary stiffness although such frames would lack the favorable hoop strength property of the circular or oval shaped frames.

The frame 14 is preferably attached to the fabric by insert molding. The mesh fabric may be surface treated with a carbon dioxide plasma etch prior to molding which may enhance the union of the mesh and the ring when formed from dissimilar materials. Alternatively, the ring and mesh may be ultrasonically welded, heat sealed or adhesively bonded. The frame may be overlayed onto a surface of the mesh fabric or may be joined to the fabric edges.

The fabric 12 preferably is formed of a sheet of knitted polypropylene monofilament mesh fabric such as MARLEX mesh available from C.R. Bard, Inc. When implanted, the polypropylene mesh stimulates an inflammatory reaction which promotes rapid tissue ingrowth into and around the mesh structure. Alternatively, other surgical materials which are suitable for tissue reinforcement and/or defect closure may be utilized including PROLENE, MERSELENE, DACRON, TEFLON textile based meshes, microporous polypropylene sheeting (CELGARD), and expanded PTFE (GORETEX). Absorbable meshes, including polyglactin (VICRYL) and polyglycolic acid (DEXON), may be suitable for applications involving temporary repair of fascial defects. It also is contemplated that the mesh fabric may be formed from monofilament or multifilament yarns and that woven, molded and other recognized methods of forming prosthetic mesh materials would be suitable.

Non-tissue infiltratable fabrics also may be supported by the ring-shaped frame. Silicone elastomer sheeting, such as SILASTIC Rx Medical Grade Sheeting (Platinum Cured) distributed by Dow Corning Corporation, would be suitable. The silicone elastomer sheeting may be reinforced with DACRON or other reinforcing materials. It is contemplated that oxidized, regenerated cellulose (Intercede(TC7)) also may have applications in the present invention.

The ring 14 may be formed from a polypropylene material or a silicone material. Other semi-rigid materials which are stiffer than the mesh fabric yet sufficiently pliable to be rolled-up in the delivery lumen also may be suitable. Alternatively, the ring may be formed by hot or cold forming a ring-shaped depression in the mesh sheet. The formed pattern is more rigid than the nonformed body portion of the mesh, providing a stiffer implant with improved handleability. Building up the edges of the body portion with additional mesh material, for example, by superposing rings of mesh around the body portion or heat setting folds of mesh from outlying portions of the fabric, also would increase the dimensional stability of the implant.

The implant 10 may include spaced barbs 22 for preventing migration of the implant until tissue infiltration securely anchors the mesh relative to the rupture site. The barbs grab, pierce or otherwise anchor to the tissue and include a variety of shapes as shown in FIGS. 3(a)–(i). The barbs 22 may extend perpendicularly from the implant. As illustrated, the barbs may have a semi-circular cross-sectional shape, a triangular cross-sectional shape, or a pointed distal tip. The barbs preferably are uniformly spaced about the ring and may be integrally molded with the ring.

In a representative embodiment, the implant includes a 2.125 inch diameter circular piece of die-cut MARLEX mesh knit from MARLEX polypropylene monofilament with a 0.006 inch diameter. A 0.030 inch thick and 0.28 inch wide circular polypropylene ring having a 2.125 inch outer diameter and a 1.980 inch inner diameter is insert molded to the MARLEX sheet.

Figure 4A:
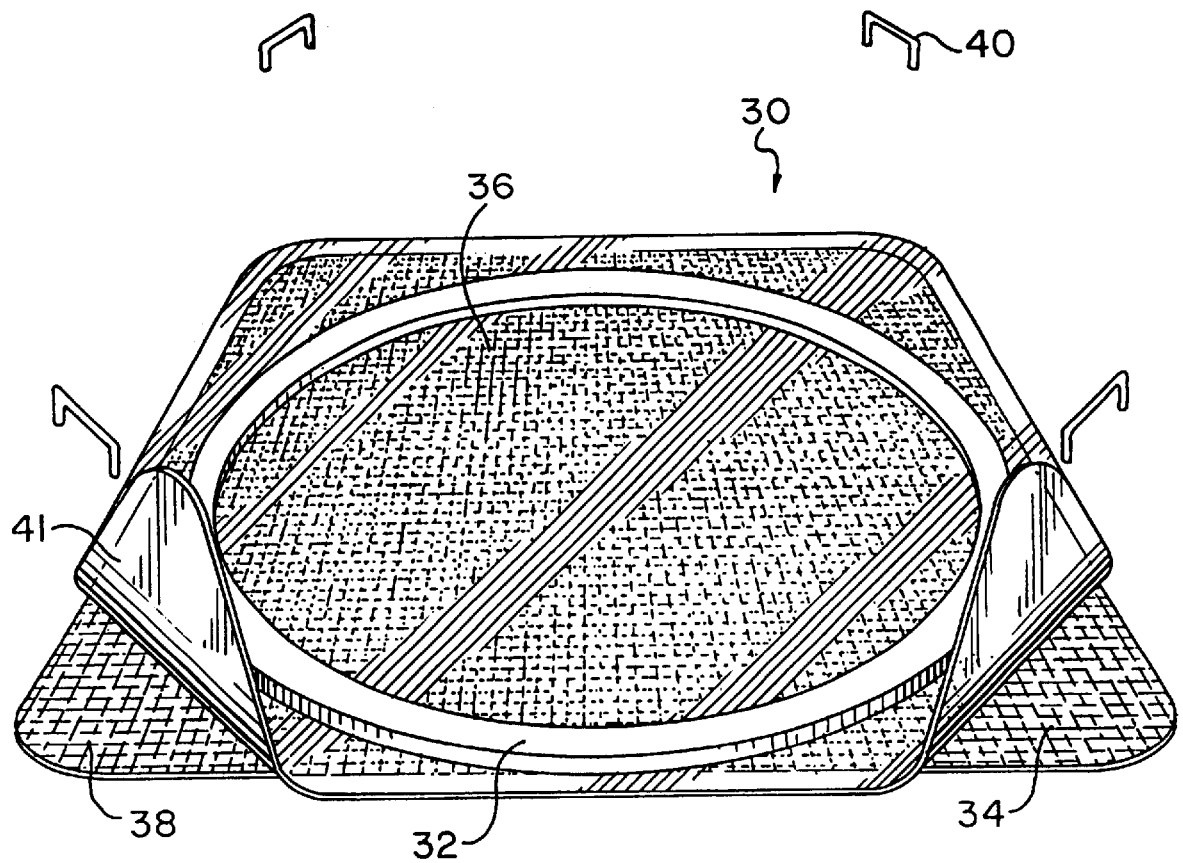
FIG. 4(a) is an illustration of an adhesion resistant implant according to the present invention.
Figure 4B:
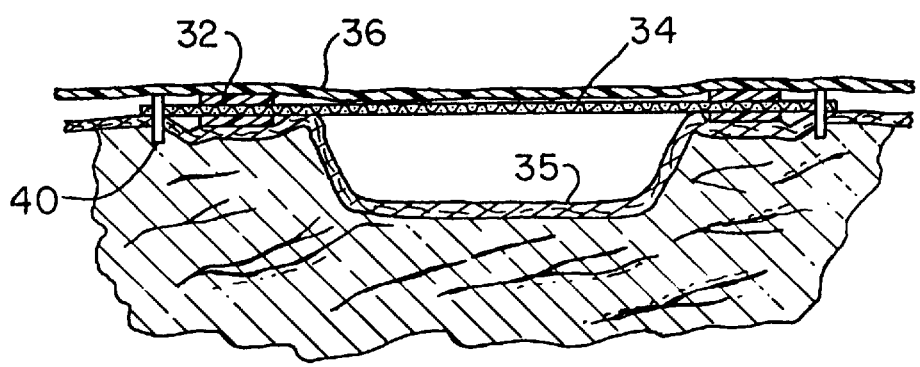
FIG. 4(b) is an illustration of an intraperitoneal repair using the implant shown in FIG. 4(a)

An implant 30 particularly suited for intraperitoneal procedures is illustrated in FIGS. 4(a)–(b) and includes a semi-rigid ring 32, a mesh fabric 34 formed of a material which stimulates an inflammatory reaction in tissue after implantation and an adhesion barrier 36 which isolates the mesh fabric 34 from sensitive tissues and organs. In an intraperitoneal procedure, the peritoneum 35 is located under the implant and therefore is not available to provide a biological barrier between the implant and the intestine. The barrier layer 36 separates the prosthetic mesh 34 from the abdominal viscera, preventing intestinal adhesion and fistulization which may result from an inflammatory reaction of the bowel and the mesh. A suitable barrier material would be a silicone elastomer, such as SILASTIC, which does not substantially stimulate adhesion formation when implanted in tissue and is significantly less likely to cause an inflammatory reaction with neighboring tissue than would a prosthetic mesh.

The portions of the MARLEX mesh fabric extending outside the ring form ears or anchoring projections 38 through which staples 40 may be driven to secure the implant to the fascia. Stapling of the ears serves the same function as the antimigration barbs, provisional anchoring of the implant until fill tissue invasion of the prosthetic mesh. The barrier layer 36 and prosthetic mesh are bonded or sewn to the ring 32. The edges 41 of the barrier outside of the ring which are not directly connected to the underlying mesh or the ring, may be lifted to allow stapling of the anchoring portions 38 to the peritoneum, provisionally anchoring the implant until sufficient tissue ingrowth holds the prosthesis in place. Upon release, the barrier margin 41 falls back over the staple and anchoring portions, providing a non-scarifying barrier between the implant and the bowel. In an alternative arrangement, the barrier and mesh may be directly attached with the ring formed along either of the mesh or barrier surfaces.

Figure 5A:
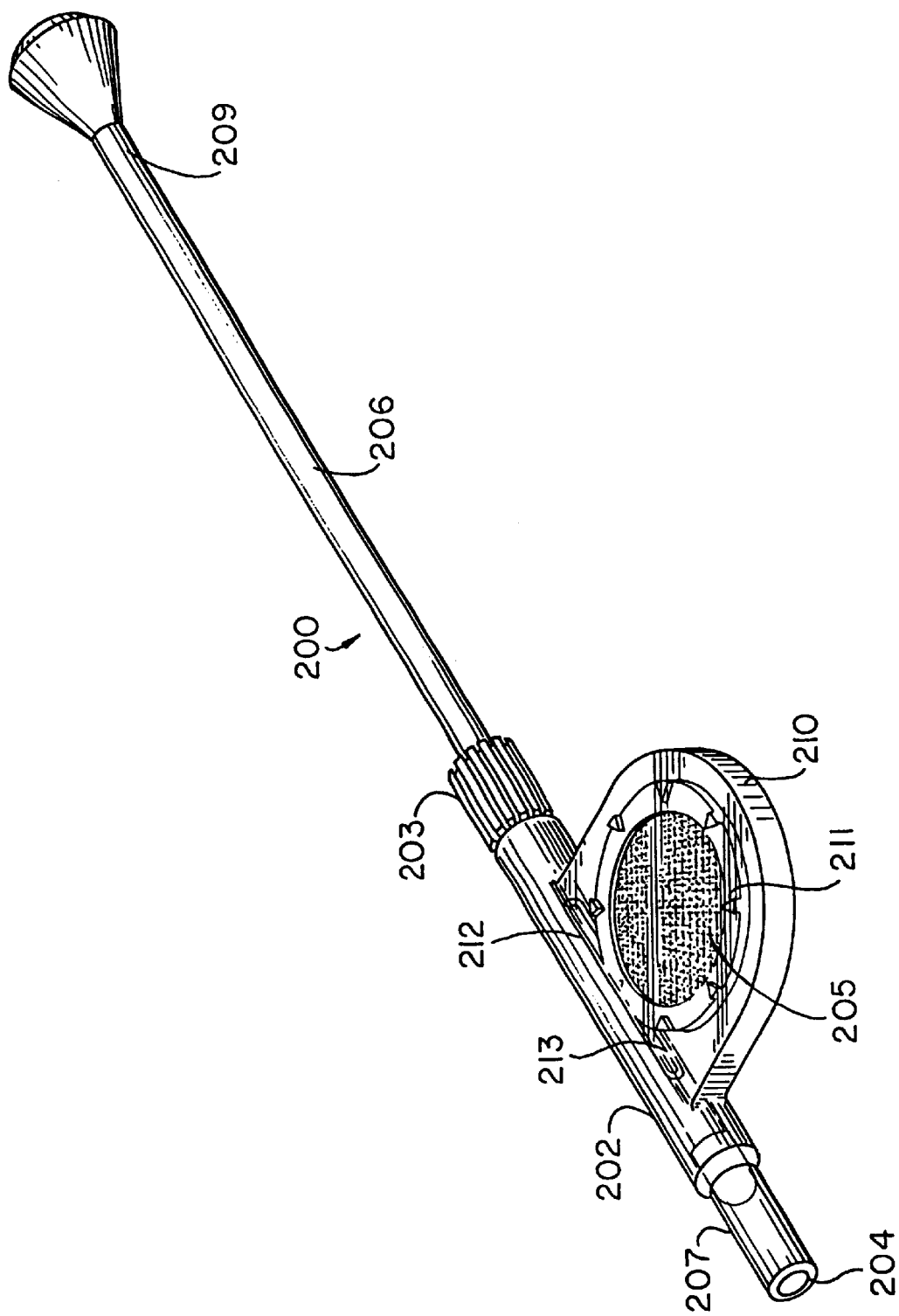
FIGS. 5(a)–(b) are illustrations of the loading and delivery tool in accordance with the present invention.
Figure 5B:
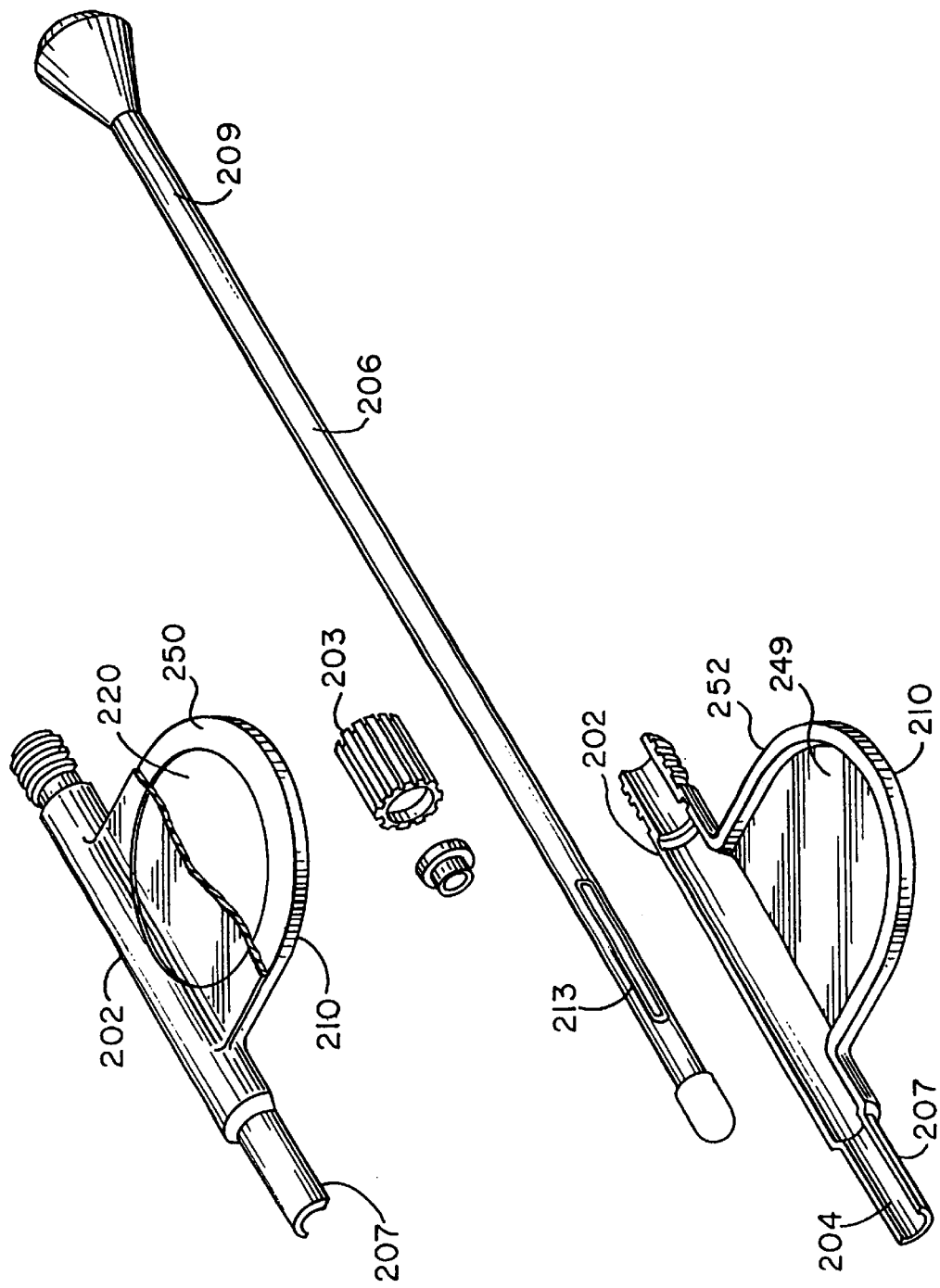

The mesh implants are too large to be inserted through the lumen of a trocar cannula. An instrument 200 for loading the implant into a narrower configuration and then delivering the implant through the trocar cannula and into the abdominal cavity is illustrated in FIGS. 5(a)–(b). By loading the implant at the surgical site, rather than providing the implant in a pre-rolled configuration within the instrument 200, a permanent setting or deformation of the implant is avoided. Such a kinked implant may not seat flush with the abdominal wall and might provide localized areas of weakness which could lead to recurrent herniation.

The loading and delivery instrument 200 includes a main body 202 having a lumen 204 for receiving and collapsing the implant 205 into a slender rolled configuration which is advanceable through the lumen of the trocar cannula. An elongated introducer shaft 206 is rotated, by turning a knurled knob 203, which winds the implant in the lumen into a narrow cylindrical configuration. After the implant is reduced in size, the stepped distal end 207 of the main body is inserted into the proximal end of the previously placed trocar cannula. The proximal end 209 of the elongated shaft (outside of the trocar cannula) is manipulated to advance the implant from the main body, through the trocar cannula and into the abdominal cavity. No longer confined by the lumen walls of the main body and the trocar cannula, the implant unfurls into its relaxed flat configuration. Rotating the shaft 206 in the direction opposite the one used in winding should facilitate deployment of the implant. Instruments inserted through additional trocar cannulae may then be manipulated by the surgeon to position the implant about the herniated area.

The main body 202 includes a uniform diameter central lumen 204 which is sized to reduce the implant to a predetermined diameter compatible with the trocar cannula lumen. A cartridge 210 extends from the main body and includes a sidewall 252, and a base 249 on which the implant, in the expanded form, is seated in readiness for loading and delivery. The cartridge 210 may be formed integral with the main body or may be removably connected thereto. A door 220 in the top 250 of the cartridge may be provided for access to the implant, for example, to check the integrity of the implant. Tabs 211 on the cartridge floor align the full-sized implant with an opening 212 in the main body.

The edge of the implant is threaded to a slot 213 at the distal end of the shaft which may be tapered to facilitate reception of the edge of the implant. A projection may be provided at the base of the slot 213 to pinch or grasp the implant, securing the implant and shaft during initial rotation. A pin extends from the knob 203 into a longitudinal groove in shaft 206, imparting rotational movement to the shaft as the knob is turned. An enlarged bulbous tip stabilizes the distal end of the shaft relative to the main body. A cap at the proximal end of the shaft serves as a mechanical stop of forward axial movement.

Figure 6:
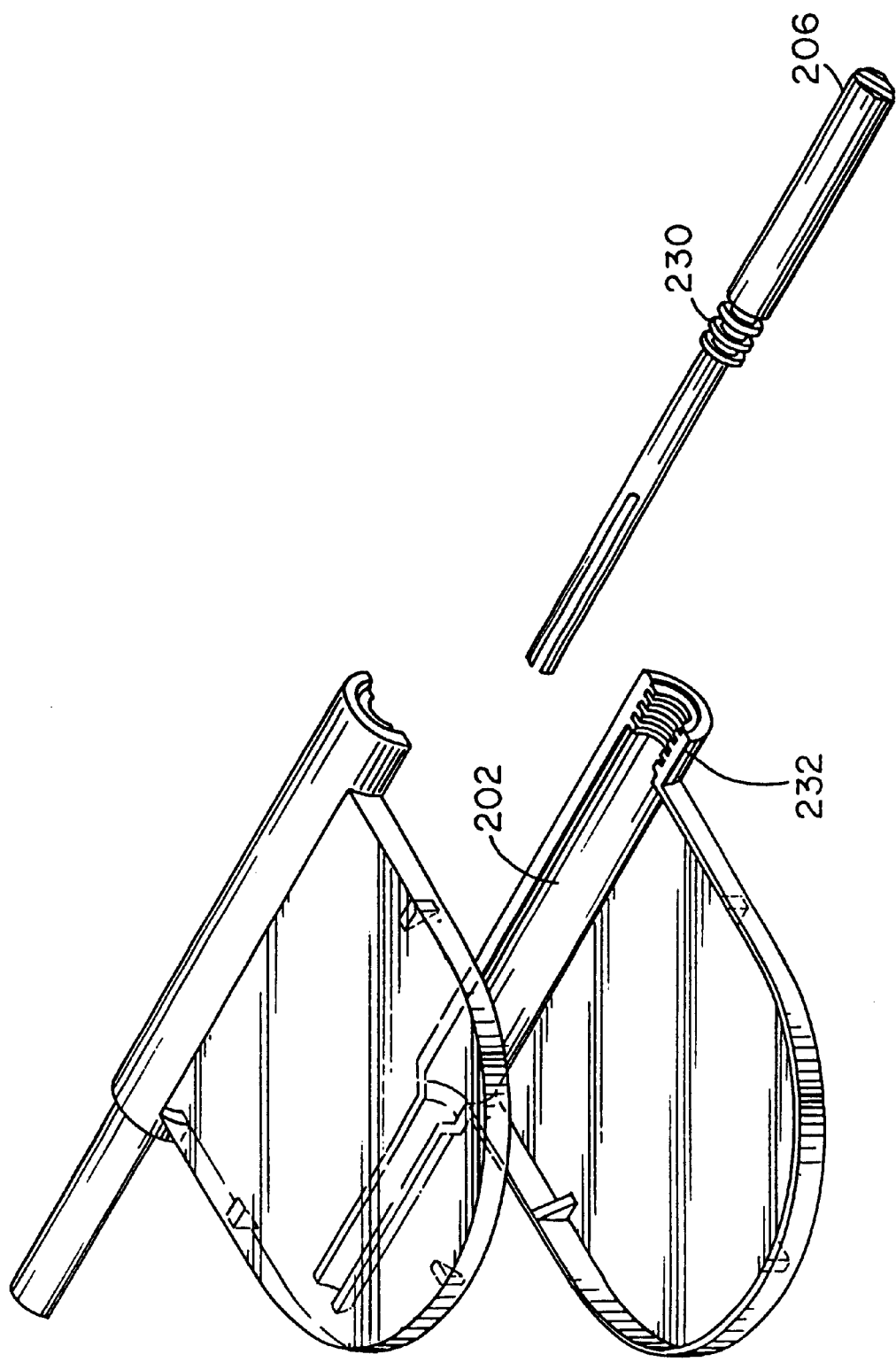
FIG. 6 is an illustration of a loading and delivery tool in accordance with the present invention with an arrangement for arresting axial movement of the shaft.

Premature axial movement of the introducer shaft may produce a helically wound implant which is too large to travel through the main body or the trocar cannula. An arrangement for arresting axial movement during rotation of the shaft is illustrated in FIG. 6. External control threads 230 in the shaft 206 are engaged to internal threads 232 in the main body 202, limiting forward movement as the implant is wound about the shaft. The number, shape and angle of the threads would vary depending upon the number of rotations of the shaft necessary to completely wind the implant.

Figure 7A:
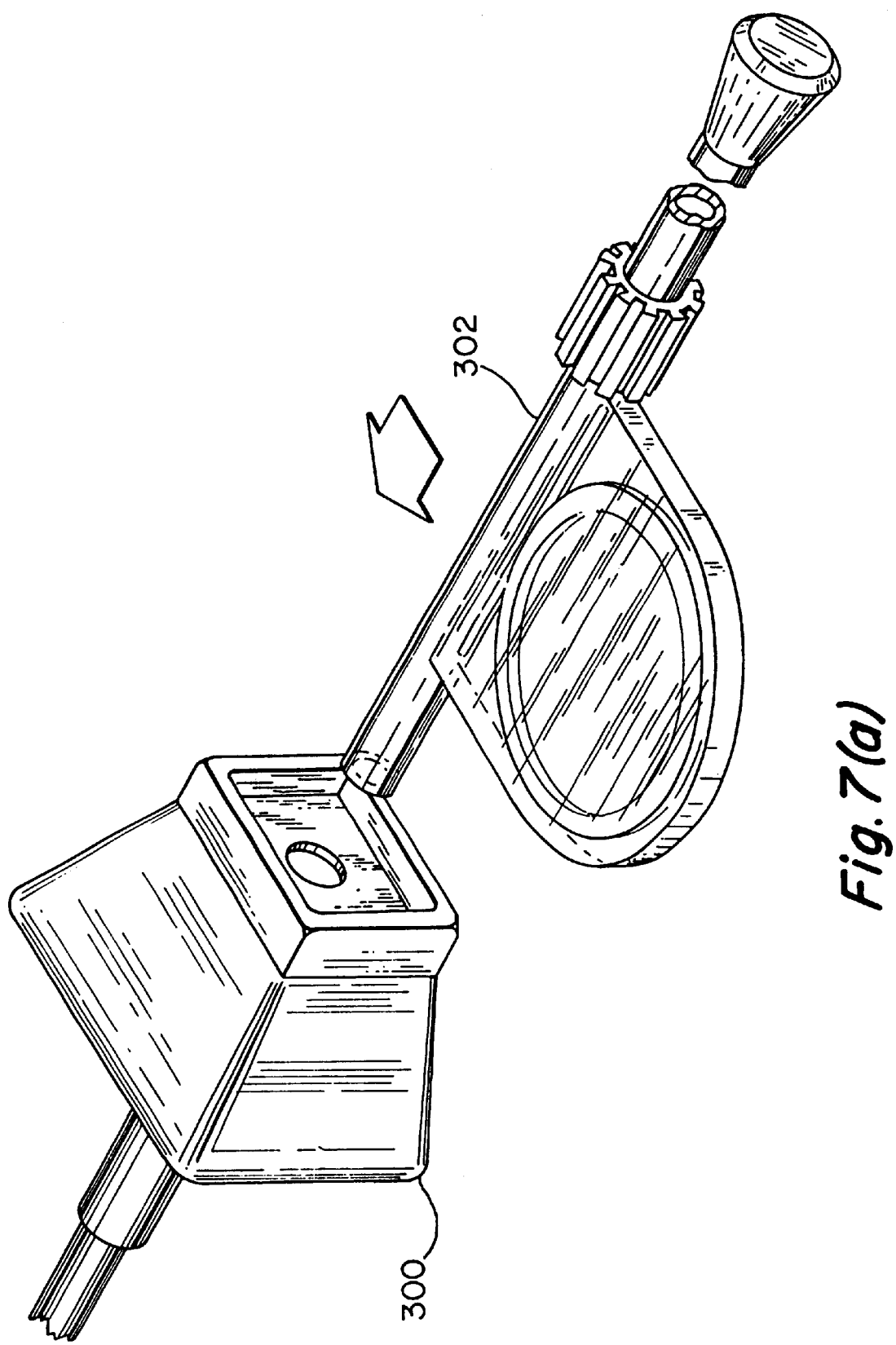
Figure 7B:
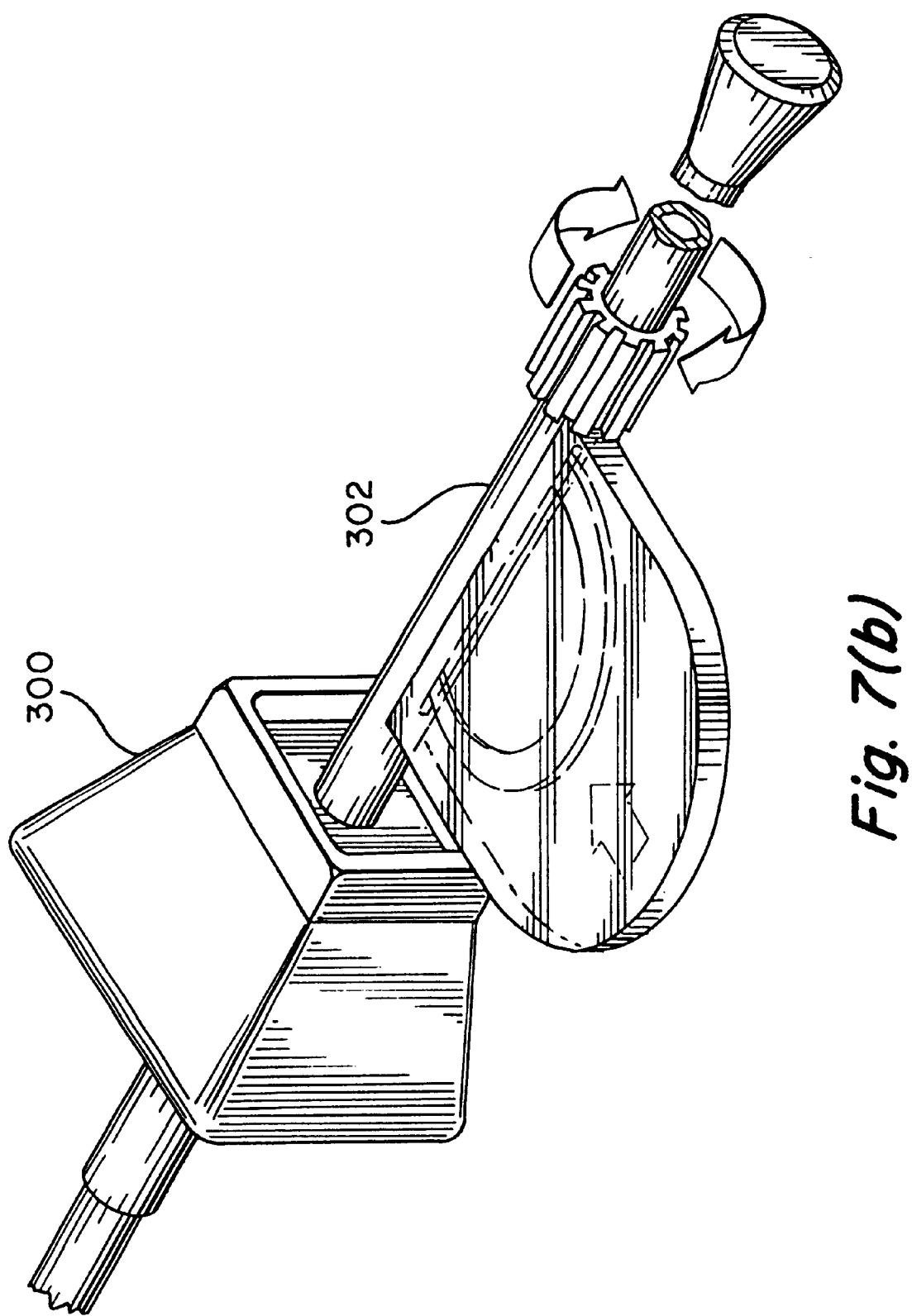

The loading and delivery of the implantable prosthesis is shown in FIGS. 7(a)–(c). While the operation of the invention is discussed in connection with the repair of an indirect inguinal hernia, a similar loading and delivery procedure would be followed for the repair of a direct inguinal hernia and other muscle wall defects. A laparoinflator is inserted through a small puncture in the abdomen near the navel. Carbon dioxide or other insufflating gas is introduced under pressure until the abdominal cavity is sufficiently inflated to allow the surgical tools to be manipulated relative to the hernia site. A sharp point of a trocar is used to form an opening through the distended abdominal wall. The trocar is withdrawn, leaving a hollow trocar cannula 300 in the newly formed passageway. A 45° laparoscope is inserted through the cannula and is connected to a television monitor which allows the surgeon to view the interior of the abdominal cavity and to assess the location, type and size of the defect. Additional cannulae are inserted through bilateral punctures in the abdominal wall. Graspers and electrocautery tools are manipulated through these cannulae to dissect the hernia sac, if indicated, and to prepare the hernia site for the implant.

A loading and delivery tool 302 carrying a suitably sized implant is removed from its sterilized packaging. The reduced diameter distal end is inserted into one of the previously emplaced trocar cannula. Rotation of the shaft draws the expanded flat implant from the cartridge into the main body lumen where it becomes wrapped around the shaft surface. The collapsed implant is guided towards the abdominal cavity by advancing the proximal end of the elongated shaft. The implant reverts to its expanded configuration upon exiting the trocar cannula. Instruments are manipulated by the surgeon to position the ring of the implant around the opening of the defect. A grasper or other tool may be used to press the ring against the muscle, securing the antimigration barbs to the healthy tissue surrounding the rupture. The inherent hoop strength of the implant prevents the mesh portion from collapsing into the void. Tissue growth through the mesh fabric extending across the opening is rapid, particularly when the mesh is formed of a material which stimulates an inflammatory reaction with tissue. In a matter of days, if not hours, tissue infiltration of the mesh secures the implant in place, repairing the herniated defect.

The present invention therefore provides an implantable prosthesis and a method and device for loading and delivering the prosthesis, amongst which are certain of the following advantages. The mesh implants provide an effective means for repairing an indirect or direct inguinal hernia by occluding the opening of the defect without requiring that the entire void be filled. The pliable prosthesis is rollable into a configuration which is small enough to be inserted through a laparoscopic cannula, yet is sufficiently resilient to revert to the normal expanded configuration which is required to evenly cover the herniated site. The increased dimensional stability of the implant enhances handleability of the mesh fabric during laparoscopic surgery. The delivery tool provides a simple and quick system for loading and delivering the implant to the abdominal cavity at the surgical site.

It should be understood that the foregoing description of the invention is intended merely to be illustrative thereof and that other equivalents, embodiments and modifications of the invention may be apparent to those skilled in the art.

What is claimed is:

1. An implantable prosthesis for occluding the opening of a muscle or tissue defect, comprising:
    a flexible, generally flat patch of implantable material including a body portion constructed and arranged to cover the defect opening when positioned thereagainst; and
    a plurality of barbs disposed on said patch of implantable material and extending at spaced locations from said patch of implantable material, wherein said plurality of spaced barbs prevent migration of said implantable prosthesis after implantation.

2. The implantable prosthesis recited in claim 1, wherein said patch of implantable material includes a mesh fabric having a plurality of interstices constructed and arranged to allow tissue ingrowth so that the mesh becomes secured to neighboring tissue.

3. The implantable prosthesis recited in claim 1, wherein said plurality of spaced barbs extend perpendicularly from said patch of implantable material.

4. The implantable prosthesis recited in claim 1, wherein said plurality of spaced barbs have a semi-circular cross-sectional shape.

5. The implantable prosthesis recited in claim 1, wherein said plurality of spaced barbs have a triangular cross-sectional shape.

6. The implantable prosthesis recited in claim 1, wherein said plurality of spaced barbs have a pointed distal tip.

7. The implantable prosthesis recited in claim 1, wherein said plurality of spaced barbs are uniformly spaced about said patch of implantable material.

8. The implantable prosthesis recited in claim 1, wherein said patch further includes an implantable base attached to and circumscribing said body portion, said implantable base being constructed and arranged to urge said body portion toward a generally flat configuration.

9. An implantable prosthesis for occluding the opening of a muscle or tissue defect, comprising:
    an implantable material including a body portion constructed and arranged to cover the defect opening when positioned thereagainst;
    an implantable base attached to and circumscribing said body portion, said implantable base being constructed and arranged to urge said body portion toward a non-tubular configuration; and
    a plurality of barbs disposed at spaced locations on said implantable base and extending from said implantable base, wherein said plurality of spaced barbs prevent migration of said implantable prosthesis after implantation.

10. The implantable prosthesis recited in claim 9, wherein said plurality of spaced barbs are integrally formed with said implantable base.

11. The implantable prosthesis recited in claim 9, wherein said plurality of spaced barbs are uniformly spaced about said implantable base.

12. The implantable prosthesis recited in claim 9, wherein said plurality of spaced barbs extend perpendicularly from said implantable base.

13. An implantable prosthesis for occluding the opening of a muscle or tissue defect, comprising:
    a flexible, generally flat patch of implantable material including a body portion constructed and arranged to cover the defect opening when positioned thereagainst; and
    a plurality of anchors disposed on said patch of implantable material and extending at spaced locations from said patch of implantable material, wherein said plurality of spaced anchors prevent migration of said implantable prosthesis after implantation.

14. The imnlantable prosthesis recited in claim 13, wherein said imnpatch of implantable material includes a mesh fabric having a plurality of interstices constructed and arranged to allow tissue ingrowth so that the mesh becomes secured to neighboring tissue.

15. The implantable prosthesis recited in claim 13, wherein said plurality of spaced anchors extend perpendicularly from said patch of implantable material.

16. The implantable prosthesis recited in claim 13, wherein said plurality of spaced anchors have a semicircular cross-sectional shape.

17. The implantable prosthesis recited in claim 13, wherein said plurality of spaced anchors have a triangular cross-sectional shape.

18. The implantable prosthesis recited in claim 13, wherein said plurality of spaced anchors have a pointed distal tip.

19. The implantable prosthesis recited in claim 13, wherein said plurality of spaced anchors are uniformly spaced about said implantable material.

20. The implantable prosthesis recited in claim 13, wherein said patch further includes an implantable base attached to and circumscribing said body portion, said implantable base being constructed and arranged to urge said body portion toward a generally flat configuration.

21. An implantable prosthesis for occluding the opening of a muscle or tissue defect, comprising:

an implantable material including a body portion constructed and arranged to cover the defect opening when positioned thereagainst;

an implantable base attached to and circumscribing said body portion, said implantable base being constructed and arranged to urge said body portion toward a non-tubular configuration; and a plurality of anchors disposed at spaced locations on said implantable base and extending from said implantable base, wherein said plurality of spaced anchors prevent migration of said implantable prosthesis after implantation.

22. The implantable prosthesis recited in claim 21, wherein said plurality of spaced anchors are integrally formed with said implantable base.

23. The implantable prosthesis recited in claim 21, wherein said plurality of spaced anchors are uniformly spaced about said implantable base.

24. The implantable prosthesis recited in claim 21, wherein said plurality of spaced anchors extend perpendicularly from said implantable base.

25. An implantable prosthesis for occluding the opening of a muscle or tissue defect, comprising:

a flexible, generally flat patch of implantable material including a body portion constructed and arranged to cover the defect opening when positioned thereagainst; and means, disposed on said patch of implantable material, for preventing migration of said implantable prosthesis after implantation.

26. The implantable prosthesis recited in claim 25, wherein said patch of implantable material includes a mesh fabric having a plurality of interstices constructed and arranged to allow tissue ingrowth so that the mesh becomes secured to neighboring tissue.

27. The implantable prosthesis recited in claim 25, wherein said patch further includes means for maintaining said body portion in a predetermined shape.

28. The implantable prosthesis recited in claim 27, wherein said means for preventing migration is disposed on said means for maintaining said body portion in the predetermined shape.

29. The implantable prosthesis recited in claim 1, consisting essentially of said patch and said plurality of spaced barbs.

30. The implantable prosthesis recited in claim 1, wherein said patch is sufficiently flexible to be rolled into a cylindrical shape.

31. The implantable prosthesis recited in claim 9, wherein said implantable base is constructed and arranged to urge said body portion toward a generally flat configuration.

32. The implantable prosthesis recited in claim 13, consisting essentially of said patch and said plurality of spaced anchors.

33. The implantable prosthesis recited in claim 13, wherein said patch is sufficiently flexible to be rolled into a cylindrical shape.

34. The implantable prosthesis recited in claim 21, wherein said implantable base is constructed and arranged to urge said body portion toward a generally flat configuration.

35. The implantable prosthesis recited in claim 25, consisting essentially of said patch and said means for preventing migration.

36. The implantable prosthesis recited in claim 25, wherein said patch is sufficiently flexible to be rolled into a cylindrical shape.

37. An implantable prosthesis for occluding the opening of a muscle or tissue defect, comprising:

an implantable material including a body portion constructed and arranged to cover the defect opening when positioned thereagainst;

means for urging said body portion toward a non-tubular configuration; and means, disposed on said means for urging, for preventing migration of said implantable prosthesis after implantation.

38. The implantable prosthesis recited in claim 37, wherein said implantable material includes a mesh fabric having a plurality of interstices constructed and arranged to allow tissue ingrowth so that said mesh fabric becomes secured to neighboring tissue.

39. The implantable prosthesis recited in claim 37, wherein said implantable material includes a flexible, generally flat patch including said body portion, said means for urging being attached to said patch and circumscribing said body portion.

40. The implantable prosthesis recited in claim 37, wherein said means for urging includes means for urging said body portion toward a generally flat configuration.

* * * * *